United States Patent
Urgell Beltran et al.

(10) Patent No.: US 8,388,986 B2
(45) Date of Patent: Mar. 5, 2013

(54) USE OF CATIONIC SURFACTANTS IN COSMETIC PREPARATIONS

(75) Inventors: Joan Baptista Urgell Beltran, Barcelona (ES); Joan Seguer Bonaventrua, Barcelona (ES)

(73) Assignee: Laboratorios Miret S.A., Barcelona (ES)

( * ) Notice: Subject to any disclaimer, the term of this patent is extended or adjusted under 35 U.S.C. 154(b) by 959 days.

(21) Appl. No.: 10/484,138

(22) PCT Filed: Aug. 9, 2001

(86) PCT No.: PCT/EP01/09198
§ 371 (c)(1),
(2), (4) Date: Jan. 16, 2004

(87) PCT Pub. No.: WO03/013453
PCT Pub. Date: Feb. 20, 2003

(65) Prior Publication Data
US 2004/0175350 A1    Sep. 9, 2004

(51) Int. Cl.
A61K 8/02 (2006.01)
(52) U.S. Cl. ...................................... 424/401
(58) Field of Classification Search .................. 424/401
See application file for complete search history.

(56) References Cited

U.S. PATENT DOCUMENTS

| | | | |
|---|---|---|---|
| 3,825,560 A | 7/1974 | Saito et al. | 260/326.45 |
| 4,389,489 A | 6/1983 | Preiss et al. | 435/280 |
| 5,093,133 A * | 3/1992 | Wisniewski et al. | 424/484 |
| 5,336,515 A | 8/1994 | Murphy et al. | 426/573 |
| 5,661,149 A | 8/1997 | King et al. | |
| 5,681,802 A | 10/1997 | Fujiwara et al. | |
| 5,780,658 A | 7/1998 | Martinez-Pardo et al. | 554/51 |
| 6,068,867 A | 5/2000 | Nussinovitch et al. | 426/102 |
| 6,238,654 B1 * | 5/2001 | Tournilhac et al. | 424/63 |
| 6,299,915 B1 | 10/2001 | Nussinovitch et al. | 426/89 |
| 7,074,447 B2 * | 7/2006 | Bonaventura et al. | 426/321 |
| 7,758,851 B2 * | 7/2010 | Urgell Beltran et al. | 424/70.19 |
| 2003/0049305 A1 | 3/2003 | Von Rymon Lipinski et al. | 424/439 |
| 2004/0166082 A1 | 8/2004 | Urgell-Beltran et al. | 434/70.21 |
| 2004/0175350 A1 | 9/2004 | Urgell Beltran et al. | 424/70.27 |
| 2004/0265443 A1 | 12/2004 | Beltran et al. | 426/321 |
| 2005/0175747 A1 | 8/2005 | Seguer Bonaventura et al. | 426/323 |
| 2006/0003421 A1 | 1/2006 | Markussen et al. | 435/69.1 |

FOREIGN PATENT DOCUMENTS

| | | |
|---|---|---|
| EP | 0 485 616 | 5/1992 |
| EP | 0 500 332 | 8/1992 |
| EP | 0 749 960 A1 | 12/1996 |
| ES | EP0749960 A1 * | 12/1996 |
| GB | 1 352 420 | 5/1974 |
| JP | 58-039651 | 3/1983 |
| JP | 59164704 | 9/1984 |
| JP | 03291211 | 12/1991 |
| JP | 09188605 | 7/1997 |
| JP | 09-255518 | 9/1997 |
| JP | 09286712 | 11/1997 |
| JP | 10045557 | 2/1998 |
| WO | 94/07377 | 4/1994 |
| WO | 94/19026 | 9/1994 |
| WO | 94/19027 | 9/1994 |
| WO | 96/21642 | 7/1996 |
| WO | 97/30964 | 8/1997 |
| WO | 01/49121 | 7/2001 |

OTHER PUBLICATIONS

Chemical Abstracts No. 117:114020; *New Lipoproteic Surfactants*;(1991).
Chemical Abstracts No. 107:79974; *Cationic Surfactants with Antimicrobial Activity*; (1985).
Chemical Abstracts No. 103:179968; *A Comparative Study on Surface-Active and Antimicrobila Properties of Some N.alpha-lauroyl-L-alpha, omega-dibasic amino acid derivatives* (1985).
Chemical Abstracts No. 99:122920; *N.alpha-acyl-L-alkylaminoguanidinic acids and their salts as surfactants with antimicrobial action* (1983).
Chemical Abstracts Service, Columbus, Ohio, US; Garcia Dominguez, J. et al.: "Cationic Surfactants With Antimicrobial Activity" retrieved from STN Database Accession No. 107:79974, XP002196810, Abstract and ES 530 051 A (Consejo Superior De Investigaciones Cientificas, Spain) May 1, 1995.

(Continued)

Primary Examiner — Jeffrey S Lundgren
Assistant Examiner — Chris Simmons
(74) Attorney, Agent, or Firm — Renner, Otto, Boisselle & Sklar, LLP

(57) ABSTRACT

The invention relates to a new use of cationic surfactants derived from the condensation of fatty acids and esterified dibasic amino acids, according to the following formula:

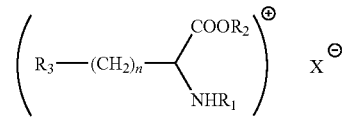

where: $X^-$ is $Br^-$, $Cl^-$, or $HSO_4^-$. R1: is linear alkyl chain from a saturated fatty acid, or hydroxyacid from 8 to 14 atoms of carbon bonded to the α-amino acid group through amidic bond. R2: is a lineal or branched alkyl chain from 1 to 18 carbon atoms or aromatic, and R3: is:

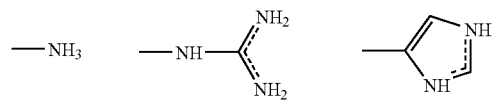

and n can be from 0 to 4. This class of compounds turned out to be highly suitable for use as preservatives in cosmetic or dermatological preparations. A particularly suitable compound is the ethyl ester of the lauramide of arginine hydrochloride (LAE).

7 Claims, No Drawings

OTHER PUBLICATIONS

Chemical Abstracts Service, Columbus, Ohio, US; Garcia Dominguez, J. J. et al.: "N.alpha.-Acyl-L-alkylaminoguanidinic Acids and Their Salts as Surfactants With Antimicrobial Action" retrieved from STN Database Accession No. 99:122920, XP002196912, Abstract and ES 512 643 A (Asociacion De Investigacion De Detergentes, Spain) Feb. 16, 1983.

Infante et al., Surface Active Molecules: Preparation and Properties of Long Chain Nα-Acyl-L-α-Amino-ω-Guanidine Alkyl Acid Derivatives; International Journal of Cosmetic Science 6, 1984, pp. 275-282.

Infante et al., A Comparative Study on Surface Active and Antimicrobial Properties of Some Nα-Lauroyl-Lα, ωDibasic Aminoacids Derivatives; Fette Seifen Anstrichmittel, No. 8, 1985, pp. 309-313.

Garcia Dominguez et al.; Monocapas De Algunos N-α-Acil Aminoacidos Antimicrobianos En Soluciones De NaCl; Anales de Quimica, vol. 82, 1986, pp. 413-418, English Abstract Only.

Infante et al.; The Influence of Steric Configuration of Some Nα-Lauroyl Amino-Acid Derivatives on Their Antimicrobial Activity; Fette Seifen Anstrichmittel, 88, No. 3, 1986, pp. 108-110.

Molinero et al.; Synthesis and Properties of Nα-Lauroyl-L-Argine Dipeptides From Collagen; JAOCS, vol. 65, No. 6, 1988, 4 pages.

Vinardell et al.; Comparative Ocular Test of Lipopeptidic Surfactants; International Journal of Cosmetic Science 12, 1990, pp. 13-20.

Kunieda et al.; Reversed Vesicles From Biocompatible Surfactants, Advanced Materials, No. 4, 1992, pp. 291-293.

Infante et al.; Sintesis Y Propiedades De Tensioactivos Cationicos Derivados De Arginina; Anales de Química, vol. 88, 1992, pp. 542-547, English Abstract Only.

Fördedal et al.; Lipoamino Acid Association in the System Nα-Lauroyl-L-Arginine Methyl Ester-1-Pentanol-Water as Studied by Dielectric Spectroscopy; Colloids and Surfaces A: Physiochemical and Engineering Aspects, 79, 1993, pp. 81-88.

Infante et al., Non-Conventional Surfactants From Amino Acids and Glycolipids: Structure, Preparation and Properties; Colloids and Surfaces A: Physicochemical and Engineering Aspects 123-124, 1997, pp. 49-70.

Moran et al.; Chemical Structure/Property Relationship in Single-Chain Arginine Surfactants; Langmuir 2001, 17, pp. 5071-5075.

* cited by examiner

USE OF CATIONIC SURFACTANTS IN COSMETIC PREPARATIONS

RELATED APPLICATION DATA

This application is a national phase application under 35 U.S.C. 371 of PCT/EP01/09198, filed Aug. 9, 2001.

FIELD OF THE INVENTION

This invention relates to a novel use of cationic surfactants and preparations according to this novel use.

BACKGROUND OF THE INVENTION

Due to their composition, many cosmetic products are susceptible to act as a culture medium for microorganisms, and this can cause possible alterations to the cosmetic preparation and constitute a possible risk to human heath as well. Thus, a cosmetic composition requires good protection against microbiological contamination.

A well-known substance used for the protection against microorganisms is a cationic surfactant derived from lauric acid and arginine, in particular, the ethyl ester of the lauramide of the arginine monohydrochloride, hereafter named LAE. The chemical structure is described in the following formula:

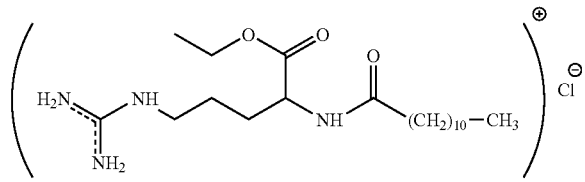

This compound is remarkable for its activity against different microorganisms, such as bacteria, fungi and yeasts and its use is known in food and feed preparations. The compound is well-known to be harmless to animals and humans. The minimum inhibitory concentrations of LAE are shown in the following table 1.

TABLE 1

| Kind | Microorganism | M.I.C. (ppm) |
|---|---|---|
| Gram + Bacteria | *Arthrobacter oxydans* ATCC 8010 | 64 |
| | *Bacillus cereus* var *mycoide* ATCC 11778 | 32 |
| | *Bacillus subtilis* ATCC 6633 | 16 |
| | *Clostridium perfringens* ATCC 77454 | 16 |
| | *Listeria monocytogenes* ATCC 7644 | 10 |
| | *Staphylococcus aureus* ATCC 6538 | 32 |
| | *Micrococcus luteus* ATCC 9631 | 128 |
| | *Lactobacillus delbrueckii* ssp *lactis* CECT 372 | 16 |
| | *Leuconostoc mesenteroides* CETC 912 | 32 |
| Gram − Bacteria | *Alcaligenes faecalis* ATCC 8750 | 64 |
| | *Bordetella bronchiseptica* ATCC 4617 | 128 |
| | *Citrobacter freundii* ATCC 22636 | 64 |
| | *Enterobacter aerogenes* CECT 689 | 32 |
| | *Escherichia coli* ATCC 8739 | 32 |
| | *Escherichia coli* 0157H7 | 20 |
| | *Klebsiella pneumoniae* var *pneumoniae* CECT 178 | 32 |
| | *Proteus mirabilis* CECT 170 | 32 |
| | *Pseudomonas aeruginosa* ATCC 9027 | 64 |
| | *Salmonella typhimurium* ATCC 16028 | 32 |
| | *Serratia marcenses* CECT 274 | 32 |
| | *Mycobacterium phlei* ATCC 41423 | 2 |

TABLE 1-continued

| Kind | Microorganism | M.I.C. (ppm) |
|---|---|---|
| Fungi | *Aspergillus niger* ATCC 14604 | 32 |
| | *Aureobasidium pullulans* ATCC 9348 | 16 |
| | *Gliocadium virens* ATCC 4645 | 32 |
| | *Chaetonium globosum* ATCC 6205 | 16 |
| | *Penicillium chrysogenum* CECT 2802 | 128 |
| | *Penicillium funiculosum* CECT 2914 | 16 |
| Yeast | *Candida albicans* ATCC 10231 | 16 |
| | *Rhodotorula rubra* CECT 1158 | 16 |
| | *Saccharomyces cerevisiae* ATCC 9763 | 32 |

DETAILED DESCRIPTION

It has now been detected that the product LAE and related compounds are particularly suitable to be used in cosmetic preparations.

The use of the invention relates to cationic surfactants derived from the condensation of fatty acids and esterified dibasic amino acids, according to the following formula:

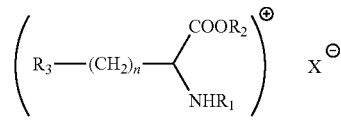

where:

$X^-$ is $Br^-$, $Cl^-$, or $HSO_4^-$ $R_1$: is a linear alkyl chain from a saturated fatty acid or hydroxyacid from 8 to 14 atoms of carbon bonded to the α-amino acid group through an amidic bond.

$R_2$: is a linear or branched alkyl chain from 1 to 18 carbon atoms or an aromatic group.

$R_3$: is:

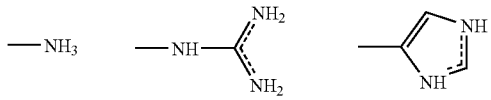

and n can be from 0 to 4.

The most preferred compound of the above class of compounds is LAE.

LAE can be used in cosmetic formulations and preparations that are applied in the epidermis, the capillary system, lips, nails, external genital organs, or in the teeth and mouth cavity mucous, in order to clean, perfume, or modify its aspect and/or change corporal smells and/or protect a good physical fitness. At the same time LAE inhibits the growth of microorganisms in the cosmetic formulations and preparations in which they are susceptible to develop, and also from the microorganisms that can be introduced by the practical use of the customer.

The compositions of the invention have a medium which is compatible with the skin, the mucous membranes, and hair. These compositions can have the classical components such as: fatty compounds such as mineral oil, animals oil, vegetal oil, synthesis and silicon oils, and also alcohols, fatty acids and waxes; organic solvents, surface active agents, solubilizers and ionic and non ionic emulsifiers, thickening agents and jellying hydrophilic agents such as carboxyvinylic polymers (e.g. carbomer), acrylic copolymers (e.g. acrylates and alkylacrylates), polyacrylamides, polysaccharides, natural gums (e.g. xanthan gum); thickening agents and jellying lipophilic agents such as modified clays (e.g. bentonite), fatty acid metallic salts, hydrophobic silica and polyethylene; perfumes and essential oils; softening agents; excipients; antioxidants; sequestering agents; opacifiers; filters; colouring compounds which may be either hydrosoluble or liposoluble, and pigments; and hydrophilic or lipophilic active ingredients. These compositions can also contain further preservatives besides the ones used according to the invention.

The proportions of the components mentioned in the previous paragraph are the ones normally used in the mentioned applications. These components have to be applied without changing the preservative system of the invention.

According to the invention the compositions can be in different cosmetic forms suitable for a topic application, such as:

a) Monophasic systems:
   Aqueous or hydroglycolic solution that contain one or more surfactants to be used for the cleaning of the skin, hair and mucous membranes;
   Aqueous, hydroalcoholic, hydroglycolic or oily solution that can contain other additives to be used in the general care and/or protection for skin and/or mucous membranes;
   Aqueous, hydroalcoholic, hydroglycolic or oily gel that can contain other additives to be used in general care and/or protection for skin and/or mucous membranes;
   Solid anhydride products that can contain other additives to be used in the general care and/or protection for skin and/or mucous membranes;

b) Biphasic systems:
   Aqueous, hydroalcoholic, hydroglycolic or oily gel that can contain other additives to be used in general care and/or protection for skin and/or mucous membranes;
   Solid anhydride products that can contain other additives to be used in the general care and/or protection for skin and/or mucous membranes;
   Emulsions formed by dispersion of a oil phase in a water phase (O/W) or inverse phase (W/O), to be used in general care and/or protection of the face skin, body, hands and/or mucous; cleaning and/or removal of make-up from the skin, mucous membranes, hair and/or mouth cavity; protection and/or skin care against solar radiation effects; colouring support and pigment to be applied to the skin.

c) And combinations of the other systems that form multiphasic systems, suspensions and microemulsions.

The compositions previously mentioned can be used in different forms such as foam, spray, or aerosol compositions and can contain a propulsion agent under pressure.

Thus, the compositions of the invention can have the aspect of a cream, a lotion, a milk, an emulsion, a gel or an oil for the skin, a beauty mask, a salt, a gel, a foam/spray or an oil for bath and shower, or for making up and making-up cleaner for the face and eyes and any other aspect known in the art.

The compositions according to the invention have been prepared according to the techniques well known for a person skilled in the art.

Procedure to Evaluate the Preservative Efficacy for LAE

The method is based on the *Antimicrobial Effectiveness Testing* USP 24th Edition, 1999 (pp. 1809-1811), in order to demonstrate that the antimicrobial activity of the compound aim of the patent is enough to avoid the microbial growth that could have in the storage and use of the preparation, preventing the adverse effects of the contamination (Real Farmacopea Española, 1st Edición, 1997).

This assay consists of the contamination of the protecting formulations with an inoculum mixture of $10^8$ cfu/mL concentration, for each of the microorganisms, and the determination of the number of viable cells in the time. This inoculum mixture is composed of the following microorganisms:

| | |
|---|---|
| *Pseudomonas aeruginosa* | ATCC 9027 |
| *Staphylococcus aureus* | ATCC 6538 |
| *Candida albicans* | ATCC 10231 |
| *Aspergillus niger* | ATCC 16404 |
| *Escherichia coli* | ATCC 8739 |

The cosmetic composition to be analysed is divided into sterile containers with 50 g of product for each flask. Each container is inoculated with 0.5 mL of inoculum ($10^8$ cfu/mL). The target concentration is $10^6$ cfu/mL, approximately. All the containers are kept at a temperature between 20-25° C. and are protected from light.

The level of the microbial contamination is checked at 0 hours, 7 days, 14 days and 28 days. The number of colonies is evaluated by dilution in buffer peptone with the appropriate neutraliser agent of the preservative. The culture media used for counting the microorganisms are: Soya triptone (35-37° C., 48 hours) for the determination of bacteria; Sabouraud agar with chloramphenicol for fungi and yeast (25° C., 3-5 days).

According to *Antimicrobial Effectiveness Testing* USP 24th Edition, 1999 (pp. 1809-1811), an antimicrobial preservative is considered to be effective in topically used products made with aqueous bases or vehicles, non-sterile nasal products and emulsions, including those applied to mucous membranes, if:

Not less than 2.0 logarithm reduction from the initial calculated bacteria's count is reached at 14 days and no increase from the 14 days' count at 28 days is detected; and No increase from the initial calculated count of yeast and moulds is observed.

EXAMPLES

Different examples of cosmetic preparations and formulations are provided where the product has been assayed. Theses examples are a part of the preparations and formulations assayed.

Example 1

The composition of the cosmetic formulation in oil-in-water emulsion with non-ionic surfactant, is (in g):

| | |
|---|---|
| Polysorbate 60 | 3.00 |
| Sorbitan stearate | 2.00 |
| Cetyl alcohol | 1.00 |
| Paraffinum | 3.00 |
| Isopropyl mirystate | 3.00 |
| Caprylic-caproic triglycerides | 3.00 |
| Dimethicone | 0.50 |
| Propylene glycol | 3.00 |
| Cellulose gum | 0.25 |
| Carbomer 940 | 0.10 |
| Triethanolamine | 0.10 |
| Aqua | 100 c.s.p. |

This formulation is completed with 0.20 g of LAE and its capacity of preservation is evaluated against the formulation without LAE. The results are shown in the table 2.

TABLE 2

| | Microorganism | Without LAE (cfu/mL) | With LAE (cfu/mL) |
|---|---|---|---|
| Initial | Aerobes | $2.1 \cdot 10^6$ | $1.1 \cdot 10^6$ |
| | Fungi | $1.6 \cdot 10^4$ | $1.7 \cdot 10^4$ |
| | Yeast | $3.7 \cdot 10^5$ | $5.6 \cdot 10^5$ |
| 7 days | Aerobes | $2.1 \cdot 10^6$ | $3.1 \cdot 10^3$ |
| | Fungi | $7.0 \cdot 10^2$ | $<9.9 \cdot 10^1$ |
| | Yeast | $8.2 \cdot 10^3$ | $9.5 \cdot 10^2$ |
| 14 days | Aerobes | $6.2 \cdot 10^6$ | $3.3 \cdot 10^2$ |
| | Fungi | $5.9 \cdot 10^2$ | $<9.9 \cdot 10^1$ |
| | Yeast | $4.8 \cdot 10^3$ | $4.0 \cdot 10^2$ |

At 28 days no increase has been detected from the 14 days' count.

Example 2

The composition of an oil-in-water emulsion with an ionic emulsifier, used as cosmetic formulation, is (in g):

| | |
|---|---|
| Stearic acid | 1.70 |
| Glyceryl stearate S.E. | 2.50 |
| Cetyl alcohol | 1.50 |
| Paraffinum | 3.00 |
| Isopropyl myristate | 3.00 |
| Caprylic-caproic triglycerides | 3.00 |
| Dimethicone | 0.50 |
| Propylene glycol | 3.00 |
| Cellulose gum | 0.50 |
| Triethanolamine | 1.03 |
| Aqua | 100 c.s.p. |

This formulation is completed with 0.20 g of LAE and its capacity of preservation is evaluated against the formulation without LAE. The results are shown in the table 3.

TABLE 3

| | Microorganism | Without LAE (cfu/mL) | With LAE (cfu/mL) |
|---|---|---|---|
| Initial | Aerobes | $7.4 \cdot 10^6$ | $2.7 \cdot 10^6$ |
| | Fungi | $2.0 \cdot 10^4$ | $1.4 \cdot 10^4$ |
| | Yeast | $3.6 \cdot 10^4$ | $3.6 \cdot 10^4$ |
| 7 days | Aerobes | $5.2 \cdot 10^6$ | $1.6 \cdot 10^4$ |
| | Fungi | $8.8 \cdot 10^2$ | $<9.9 \cdot 10^1$ |
| | Yeast | $4.7 \cdot 10^4$ | $1.0 \cdot 10^2$ |
| 14 days | Aerobes | $1.7 \cdot 10^7$ | $6.5 \cdot 10^2$ |
| | Fungi | $7.0 \cdot 10^2$ | $<9.9 \cdot 10^1$ |
| | Yeast | $1.0 \cdot 10^4$ | $1.0 \cdot 10^2$ |

At 28 days no increase has been detected from the 14 days' count.

Example 3

The general composition for a cosmetic formulation, in water in oil emulsion with non-ionic emulsifiers, is (in g)

| | |
|---|---|
| Cetyl Dimethicone copolyol | 3.00 |
| Isohexadecane | 6.00 |

-continued

| | |
|---|---|
| Paraffinum | 8.00 |
| Isopropyl myristate | 6.00 |
| Caprylic-caproic triglycerides | 4.00 |
| Glycerin | 5.00 |
| Sodium chloride | 0.50 |
| Aqua | 100 c.s.p. |

This formulation is completed with 0.20 g of LAE and its capacity of preservation is evaluated against the formulation without LAE. The results are shown in the Table 4.

TABLE 4

| | Microorganism | Without LAE (cfu/mL) | With LAE (cfu/mL) |
|---|---|---|---|
| Initial | Aerobes | $1.6 \cdot 10^6$ | $6.2 \cdot 10^6$ |
| | Fungi | $2.0 \cdot 10^4$ | $1.0 \cdot 10^4$ |
| | Yeast | $3.8 \cdot 10^4$ | $7.0 \cdot 10^4$ |
| 7 days | Aerobes | $1.1 \cdot 10^6$ | $1.8 \cdot 10^3$ |
| | Fungi | $5.0 \cdot 10^2$ | $<9.9 \cdot 10^1$ |
| | Yeast | $9.0 \cdot 10^2$ | $<9.9 \cdot 10^1$ |
| 14 days | Aerobes | $8.7 \cdot 10^6$ | $<9.9 \cdot 10^1$ |
| | Fungi | $3.0 \cdot 10^2$ | $<9.9 \cdot 10^1$ |
| | Yeast | $3.0 \cdot 10^2$ | $<9.9 \cdot 10^1$ |

At 28 days no increase has been detected from the 14 days' count.

Example 4

The composition of a formulation to obtain an aqueous solution with a surfactants' mixture, is (in g):

| | |
|---|---|
| Sodium lauryl sulfate (sol. 27%) | 14.00 |
| Cocamidopropyl betaine | 6.00 |
| Disodium cocoamfoacetate | 6.00 |
| Lactic acid | 0.25 |
| Sodium chloride | 0.50 |
| Aqua | 100 c.s.p. |

This formulation is applied in bath gels.

This formulation is completed with 0.20 g of LAE and its capacity of preservation is evaluated against the formulation without LAE. The results are shown in the Table 5.

TABLE 5

| | Microorganism | Without LAE (cfu/mL) | With LAE (cfu/mL) |
|---|---|---|---|
| Initial | Aerobes | $3.6 \cdot 10^6$ | $3.3 \cdot 10^6$ |
| | Fungi | $1.6 \cdot 10^4$ | $1.9 \cdot 10^4$ |
| | Yeast | $3.9 \cdot 10^4$ | $4.6 \cdot 10^4$ |
| 7 days | Aerobes | $4.2 \cdot 10^6$ | $5.8 \cdot 10^3$ |
| | Fungi | $2.7 \cdot 10^3$ | $2.7 \cdot 10^2$ |
| | Yeast | $4.5 \cdot 10^3$ | $<9.9 \cdot 10^1$ |
| 14 days | Aerobes | $5.5 \cdot 10^6$ | $<9.9 \cdot 10^1$ |
| | Fungi | $3.4 \cdot 10^3$ | $<9.9 \cdot 10^1$ |
| | Yeast | $5.9 \cdot 10^3$ | $<9.9 \cdot 10^1$ |

At 28 days no increase has been detected from the 14 days' count.

Example 5

The composition of a formulation to obtain an aqueous solution with a surfactants' mixture, is (in g):

| | |
|---|---|
| Sodium lauryl sulfate (sol. 27%) | 14.00 |
| Cocamidopropyl betaine | 6.00 |
| Disodium lauryl sulfosuccinate | 6.00 |
| Lactic acid | 0.25 |
| Sodium chloride | 0.50 |
| Aqua | 100 c.s.p. |

This formulation is applied in bath gels.

This formulation is completed with 0.20 g of LAE and its capacity of preservation is evaluated against the formulation without LAE. The results are shown in the Table 6.

TABLE 6

| | Microorganism | Without LAE (cfu/mL) | With LAE (cfu/mL) |
|---|---|---|---|
| Initial | Aerobes | $8.6 \cdot 10^6$ | $6.7 \cdot 10^6$ |
| | Fungi | $1.1 \cdot 10^4$ | $1.4 \cdot 10^4$ |
| | Yeast | $3.2 \cdot 10^4$ | $3.6 \cdot 10^4$ |
| 7 days | Aerobes | $3.9 \cdot 10^7$ | $4.8 \cdot 10^2$ |
| | Fungi | $1.6 \cdot 10^3$ | $<9.9 \cdot 10^1$ |
| | Yeast | $3.1 \cdot 10^3$ | $<9.9 \cdot 10^1$ |
| 14 days | Aerobes | $3.3 \cdot 10^6$ | $1.3 \cdot 10^2$ |
| | Fungi | $8.3 \cdot 10^3$ | $<9.9 \cdot 10^1$ |
| | Yeast | $3.9 \cdot 10^4$ | $<9.9 \cdot 10^1$ |

At 28 days no increase has been detected from the 14 days' count.

Example 6

The composition of a formulation to obtain a hydroalcoholic gel, is (in g):

| | |
|---|---|
| Hydroxyethyl cellulose | 0.40 |
| Carbomer 940 | 0.40 |
| Glycerin | 8.00 |
| Alcohol denat | 30.00 |
| PEG 40 hydrogenated castor oil | 1.50 |
| Parfum | 0.75 |
| Triethanolamine | 0.25 |
| Aqua | 100 c.s.p. |

This formulation is applied in lotions for after-shaving skin care.

This formulation is completed with 0.20 g of LAE and its capacity of preservation is evaluated against the formulation without LAE. The results are shown in the Table 7.

TABLE 7

| | Microorganism | Without LAE (cfu/mL) | With LAE (cfu/mL) |
|---|---|---|---|
| Initial | Aerobes | $1.1 \cdot 10^6$ | $3.7 \cdot 10^6$ |
| | Fungi | $8.7 \cdot 10^4$ | $9.1 \cdot 10^4$ |
| | Yeast | $3.9 \cdot 10^4$ | $4.2 \cdot 10^4$ |
| 7 days | Aerobes | $4.6 \cdot 10^6$ | $6.9 \cdot 10^3$ |
| | Fungi | $9.1 \cdot 10^3$ | $4.1 \cdot 10^2$ |
| | Yeast | $8.6 \cdot 10^2$ | $1.6 \cdot 10^2$ |
| 14 days | Aerobes | $7.3 \cdot 10^6$ | $<9.9 \cdot 10^1$ |
| | Fungi | $1.7 \cdot 10^3$ | $<9.9 \cdot 10^1$ |
| | Yeast | $1.2 \cdot 10^3$ | $<9.9 \cdot 10^1$ |

At 28 days no increase has been detected from the 14 days' count.

Example 7

The composition of a formulation to obtain a facial tonic, is (in g):

| | |
|---|---|
| Hydroxyethyl cellulose | 0.20 |
| Caprylic-caproic triglycerides | 1.00 |
| PEG 40 hydrogenated castor oil | 6.00 |
| Lactic acid | 1.00 |
| Sodium chloride | 0.35 |
| Glycerin | 3.00 |
| Chamomilla Recutita extract | 3.00 |
| Aqua | 100 c.s.p. |

This formulation is completed with 0.20 g of LAE and its capacity of preservation is evaluated against the formulation without LAE. The results are shown in the Table 8.

TABLE 8

| | Microorganism | Without LAE (cfu/mL) | With LAE (cfu/mL) |
|---|---|---|---|
| Initial | Aerobes | $6.7 \cdot 10^6$ | $2.7 \cdot 10^6$ |
| | Fungi | $4.1 \cdot 10^4$ | $2.1 \cdot 10^4$ |
| | Yeast | $3.2 \cdot 10^4$ | $1.2 \cdot 10^4$ |
| 7 days | Aerobes | $3.7 \cdot 10^7$ | $3.6 \cdot 10^3$ |
| | Fungi | $9.1 \cdot 10^3$ | $1.3 \cdot 10^2$ |
| | Yeast | $4.2 \cdot 10^3$ | $1.1 \cdot 10^2$ |
| 14 days | Aerobes | $8.7 \cdot 10^7$ | $5.9 \cdot 10^2$ |
| | Fungi | $2.1 \cdot 10^4$ | $<9.9 \cdot 10^1$ |
| | Yeast | $1.2 \cdot 10^4$ | $<9.9 \cdot 10^1$ |

At 28 days no increase has been detected from the 14 days' count.

Example 8

The composition of a formulation to obtain a mask-up cleaner, is (in g):

| | |
|---|---|
| Stearic acid | 2.00 |
| Glyceryl stearate S.E | 2.50 |
| Cetyl alcohol | 1.50 |
| Paraffinum | 6.00 |
| Isopropyl myristate | 1.50 |
| Caprylic-caproic triglycerides | 1.50 |
| Dimethicone | 0.50 |
| Propylene glycol | 3.00 |
| Triethanolamine | 1.20 |
| Aqua | 100 c.s.p. |

This formulation is completed with 0.20 g of LAE, and the preservative capacity is evaluated and it is compared with the formulation without LAE. The results are shown in the Table 9.

TABLE 9

| | Microorganism | Without LAE (cfu/mL) | With LAE (cfu/mL) |
|---|---|---|---|
| Initial | Aerobes | $5.5 \cdot 10^6$ | $4.5 \cdot 10^6$ |
| | Fungi | $7.9 \cdot 10^4$ | $7.6 \cdot 10^4$ |
| | Yeast | $8.4 \cdot 10^4$ | $7.2 \cdot 10^4$ |
| 7 days | Aerobes | $6.5 \cdot 10^6$ | $3.8 \cdot 10^3$ |
| | Fungi | $8.2 \cdot 10^2$ | $3.5 \cdot 10^2$ |
| | Yeast | $8.8 \cdot 10^2$ | $1.8 \cdot 10^2$ |

TABLE 9-continued

|  | Microorganism | Without LAE (cfu/mL) | With LAE (cfu/mL) |
|---|---|---|---|
| 14 days | Aerobes | $9.5 \cdot 10^6$ | $6.7 \cdot 10^2$ |
|  | Fungi | $2.9 \cdot 10^3$ | $<9.9 \cdot 10^1$ |
|  | Yeast | $1.8 \cdot 10^3$ | $<9.9 \cdot 10^1$ |

At 28 days no increase has been detected from the 14 days' count.

Example 9

The composition of a formulation to obtain a fluid oil-in-water emulsion with non-ionic surfactants, is (in g):

| | |
|---|---|
| Polysorbate 60 | 3.00 |
| Sorbitan stearate | 2.00 |
| Cetyl alcohol | 0.75 |
| Paraffinum | 3.00 |
| Isopropyl myristate | 2.50 |
| Caprylic-caproic triglycerides | 2.00 |
| Dimethicone | 0.50 |
| Propylene glycol | 3.00 |
| Aqua | 100 c.s.p. |

This formulation is applied in body oil.

This formulation is completed with 0.20 g of LAE, and the preservative capacity is evaluated and it is compared with the formulation without LAE. The results are shown in the Table 10.

TABLE 10

|  | Microorganism | Without LAE (cfu/mL) | With LAE (cfu/mL) |
|---|---|---|---|
| Initial | Aerobes | $1.5 \cdot 10^6$ | $4.5 \cdot 10^6$ |
|  | Fungi | $2.6 \cdot 10^4$ | $7.6 \cdot 10^4$ |
|  | Yeast | $3.2 \cdot 10^4$ | $7.2 \cdot 10^4$ |
| 7 days | Aerobes | $4.5 \cdot 10^6$ | $7.6 \cdot 10^3$ |
|  | Fungi | $7.7 \cdot 10^3$ | $1.4 \cdot 10^2$ |
|  | Yeast | $8.4 \cdot 10^3$ | $2.3 \cdot 10^2$ |
| 14 days | Aerobes | $6.3 \cdot 10^6$ | $<9.9 \cdot 10^1$ |
|  | Fungi | $1.6 \cdot 10^4$ | $<9.9 \cdot 10^1$ |
|  | Yeast | $7.9 \cdot 10^3$ | $<9.9 \cdot 10^1$ |

At 28 days no increase has been detected from the 14 days' count.

Example 10

The composition of a toothpaste formulation is (in g):

| | |
|---|---|
| Calcium carbonate | 16.00 |
| Dicalcium phosphate | 24.00 |
| Silica | 2.00 |
| Petrolatum | 10.00 |
| Glycerine | 20.00 |
| Sodium fluoride | 0.20 |
| Hydroxyethyl cellulose | 1.00 |
| Lauroyl sarcosine | 2.00 |
| Aqua | 100 c.s.p. |

This formulation is completed with 0.20 g of LAE, and the preservative capacity is evaluated and it is compared with the formulation without LAE. The results are shown in the Table 11.

TABLE 11

|  | Microorganism | Without LAE (cfu/mL) | With LAE (cfu/mL) |
|---|---|---|---|
| Initial | Aerobes | $6.5 \cdot 10^6$ | $4.5 \cdot 10^6$ |
|  | Fungi | $9.6 \cdot 10^4$ | $5.6 \cdot 10^4$ |
|  | Yeast | $4.8 \cdot 10^4$ | $4.2 \cdot 10^4$ |
| 7 days | Aerobes | $3.5 \cdot 10^7$ | $3.3 \cdot 10^3$ |
|  | Fungi | $1.6 \cdot 10^4$ | $1.6 \cdot 10^2$ |
|  | Yeast | $5.2 \cdot 10^3$ | $1.2 \cdot 10^2$ |
| 14 days | Aerobes | $6.5 \cdot 10^7$ | $8.0 \cdot 10^2$ |
|  | Fungi | $1.7 \cdot 10^4$ | $<9.9 \cdot 10^1$ |
|  | Yeast | $4.8 \cdot 10^3$ | $<9.9 \cdot 10^1$ |

At 28 days no increase has been detected from the 14 days' count.

Example 11

The composition of a formulation to obtain an aqueous solution with surfactants, is (in g):

| | |
|---|---|
| Sodium lauryl sulfate (sol. 27%) | 12.00 |
| Cocamidopropyl betaine | 5.00 |
| Disodium cocoamfoacetate | 5.00 |
| Polyquaternium11 | 1.00 |
| Lactic acid | 0.25 |
| Sodium chloride | 0.50 |
| Aqua | 100 c.s.p. |

This formulation is applied in shampoos cosmetic formulations.

This formulation is completed with 0.20 g of LAE, and the preservative capacity is evaluated and it is compared with the formulation without LAE. The results are shown in the Table 12.

TABLE 12

|  | Microorganism | Without LAE (cfu/mL) | With LAE (cfu/mL) |
|---|---|---|---|
| Initial | Aerobes | $3.7 \cdot 10^6$ | $3.3 \cdot 10^6$ |
|  | Fungi | $7.6 \cdot 10^4$ | $9.6 \cdot 10^4$ |
|  | Yeast | $3.2 \cdot 10^4$ | $4.2 \cdot 10^4$ |
| 7 days | Aerobes | $5.9 \cdot 10^6$ | $4.8 \cdot 10^3$ |
|  | Fungi | $9.6 \cdot 10^2$ | $1.1 \cdot 10^2$ |
|  | Yeast | $4.9 \cdot 10^3$ | $1.2 \cdot 10^2$ |
| 14 days | Aerobes | $6.3 \cdot 10^6$ | $7.0 \cdot 10^2$ |
|  | Fungi | $1.1 \cdot 10^3$ | $<9.9 \cdot 10^1$ |
|  | Yeast | $5.2 \cdot 10^3$ | $<9.9 \cdot 10^1$ |

At 28 days no increase has been detected from the 14 days' count.

Example 12

The composition of a formulation to obtain an oil-in-water emulsion with non-ionic surfactants, is (in g):

| | |
|---|---|
| Glyceryl stearate + PEG 100 stearate | 4.00 |
| Cetyl alcohol + sodium cetyl sulfate | 2.00 |
| Caprylic-caproic triglycerides | 4.00 |
| Isopropyl mirystate | 2.50 |
| Paraffinum | 2.00 |
| Dimethicone | 0.50 |
| Glycerin | 3.00 |
| Wheat (triticum vulgare) germ protein | 2.00 |
| Aqua | 100 c.s.p. |

This formulation is applied in a face cream for skin care.

This formulation is completed with 0.20 g of LAE and its capacity of preservation is evaluated against the formulation without LAE. The results are shown in the Table 13.

TABLE 13

|  | Microorganism | Without LAE (cfu/mL) | With LAE (cfu/mL) |
|---|---|---|---|
| Initial | Aerobes | $3.3 \cdot 10^6$ | $1.1 \cdot 10^6$ |
|  | Fungi | $1.6 \cdot 10^4$ | $1.7 \cdot 10^4$ |
|  | Yeast | $2.2 \cdot 10^4$ | $3.2 \cdot 10^4$ |
| 7 days | Aerobes | $4.3 \cdot 10^6$ | $3.7 \cdot 10^4$ |
|  | Fungi | $1.9 \cdot 10^2$ | $8.7 \cdot 10^2$ |
|  | Yeast | $2.5 \cdot 10^2$ | $9.2 \cdot 10^2$ |
| 14 days | Aerobes | $4.3 \cdot 10^6$ | $1.9 \cdot 10^3$ |
|  | Fungi | $1.8 \cdot 10^2$ | $<9.9 \cdot 10^1$ |
|  | Yeast | $2.9 \cdot 10^2$ | $<9.9 \cdot 10^1$ |

At 28 days no increase has been detected from the 14 days' count.

Example 13

The composition of a formulation to obtain an oil-in-water emulsion with non-ionic surfactants, is (in g):

| Polysorbate 60 | 3.00 |
|---|---|
| Sorbitan stearate | 2.00 |
| Cetyl alcohol | 2.50 |
| Paraffinum | 2.00 |
| Caprylic-caproic triglycerides | 2.00 |
| Ethyl hexyl methoxycinnamate | 5.00 |
| Benzophenone 3 | 1.00 |
| Dimethicone | 0.50 |
| Propylene glycol | 3.00 |
| Aqua | 100 c.s.p. |

This formulation is applied in a sun protector cosmetic formulator.

This formulation is completed with 0.20 g of LAE and its capacity of preservation is evaluated against the formulation without LAE. The results are shown in the Table 14.

TABLE 14

|  | Microorganism | Without LAE (cfu/mL) | With LAE (cfu/mL) |
|---|---|---|---|
| Initial | Aerobes | $4.4 \cdot 10^6$ | $3.1 \cdot 10^6$ |
|  | Fungi | $5.7 \cdot 10^4$ | $4.9 \cdot 10^4$ |
|  | Yeast | $2.7 \cdot 10^4$ | $3.8 \cdot 10^4$ |
| 7 days | Aerobes | $6.3 \cdot 10^6$ | $8.4 \cdot 10^3$ |
|  | Fungi | $5.1 \cdot 10^2$ | $2.7 \cdot 10^2$ |
|  | Yeast | $2.3 \cdot 10^2$ | $4.2 \cdot 10^2$ |
| 14 days | Aerobes | $7.2 \cdot 10^6$ | $7.5 \cdot 10^2$ |
|  | Fungi | $5.9 \cdot 10^2$ | $<9.9 \cdot 10^1$ |
|  | Yeast | $2.8 \cdot 10^2$ | $<9.9 \cdot 10^1$ |

At 28 days no increase has been detected from the 14 days' count.

Example 14

The composition of a formulation to obtain an oil-in-water emulsion with non-ionic surfactants is (in g):

| Cetyl Dimethicone copolyol | 3.00 |
|---|---|
| Isohexadecane | 4.00 |
| Paraffinum | 5.00 |
| Isopropyl myristate | 3.00 |
| Caprylic-caproic triglycerides | 3.00 |
| Ethyl hexyl methoxycinnamate | 5.00 |
| Benzophenone 3 | 1.00 |
| Glycerin | 3.00 |
| Sodium chloride | 0.50 |
| Aqua | 100 c.s.p. |

This formulation is applied in a sun protector cosmetic product.

This formulation is completed with 0.20 g of LAE, and the preservative capacity is evaluated and it is compared with the formulation without LAE. The results are shown in the Table 15.

TABLE 15

|  | Microorganism | Without LAE (cfu/mL) | With LAE (cfu/mL) |
|---|---|---|---|
| Initial | Aerobes | $2.8 \cdot 10^6$ | $1.4 \cdot 10^6$ |
|  | Fungi | $5.5 \cdot 10^4$ | $5.3 \cdot 10^4$ |
|  | Yeast | $7.7 \cdot 10^4$ | $7.9 \cdot 10^4$ |
| 7 days | Aerobes | $4.4 \cdot 10^6$ | $9.4 \cdot 10^2$ |
|  | Fungi | $8.6 \cdot 10^2$ | $6.7 \cdot 10^2$ |
|  | Yeast | $8.3 \cdot 10^2$ | $4.5 \cdot 10^2$ |
| 14 days | Aerobes | $7.2 \cdot 10^6$ | $8.7 \cdot 10^2$ |
|  | Fungi | $5.8 \cdot 10^2$ | $<9.9 \cdot 10^1$ |
|  | Yeast | $7.9 \cdot 10^2$ | $<9.9 \cdot 10^1$ |

At 28 days no increase has been detected from the 14 days' count.

Example 15

The composition of a formulation to obtain an emulsion for hands care, is (in g):

| Cetyl alcohol + ceteareth 20 | 6.00 |
|---|---|
| Isopropyl myristate | 2.00 |
| Caprylic-caproic triglycerides | 1.00 |
| Dimethicone | 1.00 |
| Benzophenone 3 | 1.00 |
| Glycerin | 6.00 |
| Carbomer 940 | 0.10 |
| Triethanolamine | 0.10 |
| Aqua | 100 c.s.p. |

This formulation is completed with 0.20 g of LAE, and the preservative capacity is evaluated and it is compared with the formulation without LAE. The results are shown in the Table 16.

TABLE 16

|  | Microorganism | Without LAE (cfu/mL) | With LAE (cfu/mL) |
|---|---|---|---|
| Initial | Aerobes | $4.5 \cdot 10^6$ | $4.4 \cdot 10^6$ |
|  | Fungi | $6.1 \cdot 10^4$ | $5.8 \cdot 10^4$ |
|  | Yeast | $8.8 \cdot 10^4$ | $8.6 \cdot 10^4$ |
| 7 days | Aerobes | $7.4 \cdot 10^6$ | $3.3 \cdot 10^3$ |
|  | Fungi | $7.8 \cdot 10^2$ | $8.7 \cdot 10^2$ |
|  | Yeast | $8.9 \cdot 10^2$ | $7.2 \cdot 10^2$ |
| 14 days | Aerobes | $4.4 \cdot 10^6$ | $<9.9 \cdot 10^1$ |
|  | Fungi | $9.8 \cdot 10^2$ | $<9.9 \cdot 10^1$ |
|  | Yeast | $1.2 \cdot 10^3$ | $<9.9 \cdot 10^1$ |

At 28 days no increase has been detected from the 14 days' count.

The invention claimed is:

1. A cosmetic or dermatological composition comprising: (a) a cosmetic or dermatological preparation in the form of an oil-in-water emulsion; and (b) a preservative comprising the cationic surfactant ethyl ester of the lauramide of arginine hydrochloride (LAE), the composition having the following formulation (in g):

| | |
|---|---|
| Polysorbate 60 | 3.00 |
| Sorbitan stearate | 2.00 |
| Cetyl alcohol | 1.00 |
| Paraffinum | 3.00 |
| Isopropyl myristate | 3.00 |
| Caprylic-caproic triglycerides | 3.00 |
| Dimethicone | 0.50 |
| Propylene glycol | 3.00 |
| Cellulose gum | 0.25 |
| Carbomer 940 | 0.10 |
| Triethanolamine | 0.10 |
| Water | 100 c.s.p. | the formulation being completed with 0.20 g of LAE.

2. A cosmetic or dermatological composition comprising: (a) a cosmetic or dermatological preparation in the form of an oil-in-water emulsion; and (b) a preservative comprising the cationic surfactant ethyl ester of the lauramide of arginine hydrochloride (LAE), the composition having the following formulation (in g):

| | |
|---|---|
| Stearic acid | 1.70 |
| Glyceryl stearate SE | 2.50 |
| Cetyl alcohol | 1.50 |
| Paraffinum | 3.00 |
| Isopropyl myristate | 3.00 |
| Caprylic-caproic triglycerides | 3.00 |
| Dimethicone | 0.50 |
| Propylene glycol | 3.00 |
| Cellulose gum | 0.50 |
| Triethanolamine | 1.03 |
| Water | 100 c.s.p. | the formulation being completed with 0.20 g of LAE.

3. A cosmetic or dermatological composition comprising: (a) a cosmetic or dermatological preparation in the form of an oil-in-water emulsion; and (b) a preservative comprising the cationic surfactant ethyl ester of the lauramide of arginine hydrochloride (LAE), the composition having the following formulation (in g):

| | |
|---|---|
| Polysorbate 60 | 3.00 |
| Sorbitan stearate | 2.00 |
| Cetyl alcohol | 0.75 |
| Paraffinum | 3.00 |
| Isopropyl myristate | 2.50 |
| Caprylic-caproic triglycerides | 2.00 |
| Dimethicone | 0.50 |
| Propylene glycol | 3.00 |
| Water | 100 c.s.p. | the formulation being completed with 0.20 g of LAE.

4. A cosmetic or dermatological composition comprising: (a) a cosmetic or dermatological preparation in the form of an oil-in-water emulsion; and (b) a preservative comprising the cationic surfactant ethyl ester of the lauramide of arginine hydrochloride (LAE), the composition having the following formulation (in g):

| | |
|---|---|
| Glyceryl stearate + PEG 100 stearate | 4.00 |
| Cetyl alcohol + sodium cetyl sulfate | 2.00 |
| Caprylic-caproic triglycerides | 4.00 |
| Isopropyl myristate | 2.50 |
| Paraffinum | 2.00 |
| Dimethicone | 0.50 |
| Glycerin | 3.00 |
| Wheat (*triticum vulgare*) germ protein | 2.00 |
| Water | 100 c.s.p. | the formulation being completed with 0.20 g of LAE.

5. A cosmetic or dermatological composition comprising: (a) a cosmetic or dermatological preparation in the form of an oil-in-water emulsion; and (b) a preservative comprising the cationic surfactant ethyl ester of the lauramide of arginine hydrochloride (LAE), the composition having the following formulation (in g):

| | |
|---|---|
| Polysorbate 60 | 3.00 |
| Sorbitan stearate | 2.00 |
| Cetyl alcohol | 2.50 |
| Paraffinum | 2.00 |
| Caprylic-caproic triglycerides | 2.00 |
| Ethyl hexyl methoxycinnamate | 5.00 |
| Benzophenone 3 | 1.00 |
| Dimethicone | 0.50 |
| Propylene glycol | 3.00 |
| Water | 100 c.s.p. | the formulation being completed with 0.20 g of LAE.

6. A cosmetic or dermatological composition comprising: (a) a cosmetic or dermatological preparation in the form of an oil-in-water emulsion; and (b) a preservative comprising the cationic surfactant ethyl ester of the lauramide of arginine hydrochloride (LAE), the composition having the following formulation (in g):

| | |
|---|---|
| Cetyl Dimethicone copolyol | 3.00 |
| Isohexadecane | 4.00 |
| Paraffinum | 5.00 |
| Isopropyl myristate | 3.00 |
| Caprylic-caproic triglycerides | 3.00 |
| Ethyl hexyl methoxycinnamate | 5.00 |
| Benzophenone 3 | 1.00 |
| Glycerin | 3.00 |
| Sodium chloride | 0.50 |
| Water | 100 c.s.p. | the formulation being completed with 0.20 g of LAE.

7. A cosmetic or dermatological composition comprising: (a) a cosmetic or dermatological preparation in the form of a water-in-oil emulsion; and (b) a preservative comprising the cationic surfactant ethyl ester of the lauramide of arginine hydrochloride (LAE), the composition having the following formulation (in g):

| | |
|---|---:|
| Cetyl Dimethicone copolyol | 3.00 |
| Isohexadecane | 6.00 |
| Paraffinum | 8.00 |
| Isopropyl myristate | 6.00 |
| Caprylic-caproic triglycerides | 4.00 |
| Glycerin | 5.00 |
| Sodium chloride | 0.50 |
| Water | 100 c.s.p. | the formulation being completed with 0.20 g of LAE.

\* \* \* \* \*

UNITED STATES PATENT AND TRADEMARK OFFICE
CERTIFICATE OF CORRECTION

PATENT NO. : 8,388,986 B2  Page 1 of 1
APPLICATION NO. : 10/484138
DATED : March 5, 2013
INVENTOR(S) : Urgell Beltran et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1032 days.

Signed and Sealed this

First Day of September, 2015

Michelle K. Lee
*Director of the United States Patent and Trademark Office*